United States Patent [19]

Lupien et al.

[11] 4,103,685
[45] Aug. 1, 1978

[54] METHOD AND APPARATUS FOR EXTRAVASCULAR TREATMENT OF BLOOD

[76] Inventors: Paul J. Lupien, 686 Le Cavalier; John A. Awad, 632 Ave. Charron; Sital Moorjani, 2905 De la Providence, all of Ste-Foy, Quebec, Canada

[21] Appl. No.: 646,567

[22] Filed: Jan. 5, 1976

[51] Int. Cl.² .............................................. A61M 5/00
[52] U.S. Cl. .................................. 128/214 R; 210/28; 210/DIG. 23; 260/112 B; 23/258.5 R
[58] Field of Search ............ 128/214 C, 214 R, 214.2; 210/24 C, 28, 262, DIG. 23; 23/258.5; 424/101; 260/112 B

[56] References Cited

U.S. PATENT DOCUMENTS

| 2,842,124 | 7/1958 | James | 128/214 B |
|---|---|---|---|
| 3,448,041 | 6/1969 | Swank | 210/23 |
| 3,462,361 | 8/1969 | Greenwalt et al. | 210/23 |
| 3,492,991 | 2/1970 | Dyer | 128/214 R |
| 3,770,631 | 11/1973 | Fekete, et al. | 210/53 |
| 3,808,124 | 4/1974 | Dziobkowski et al. | 210/28 |
| 3,842,061 | 10/1974 | Anderson et al. | 424/101 X |
| 3,955,925 | 5/1976 | Proksch et al. | 260/112 X |
| 4,045,176 | 8/1977 | Proksch et al. | 260/112 B X |

OTHER PUBLICATIONS

Iverius — Jour. Biolog. Chem. vol. 247, No. 8, Apr. 1972 pp. 2607–2613.
Iverius Jour. Biol. Chem. (1971) 124: 677–683.
Srinivasan et al. — Archives of Biochem. and Biophysics, 170:334–340 (1975).

*Primary Examiner*—Dalton L. Truluck
*Attorney, Agent, or Firm*—Burgess, Ryan and Wayne

[57] ABSTRACT

There is provided a method and apparatus for the excorporeal treatment of blood of hyperlipemic anc hypercholesteremic patients whereby a portion of blood is drawn from such patients and treated with a divalent metal complex of a sulphated polysaccharide coupled to a non-sulphated polysaccharide gel having its remaining sites blocked whereby a substantial amount of the lipoproteins present in the blood are bound to the gel and then filtering the blood before returning same to the patient.

14 Claims, 5 Drawing Figures

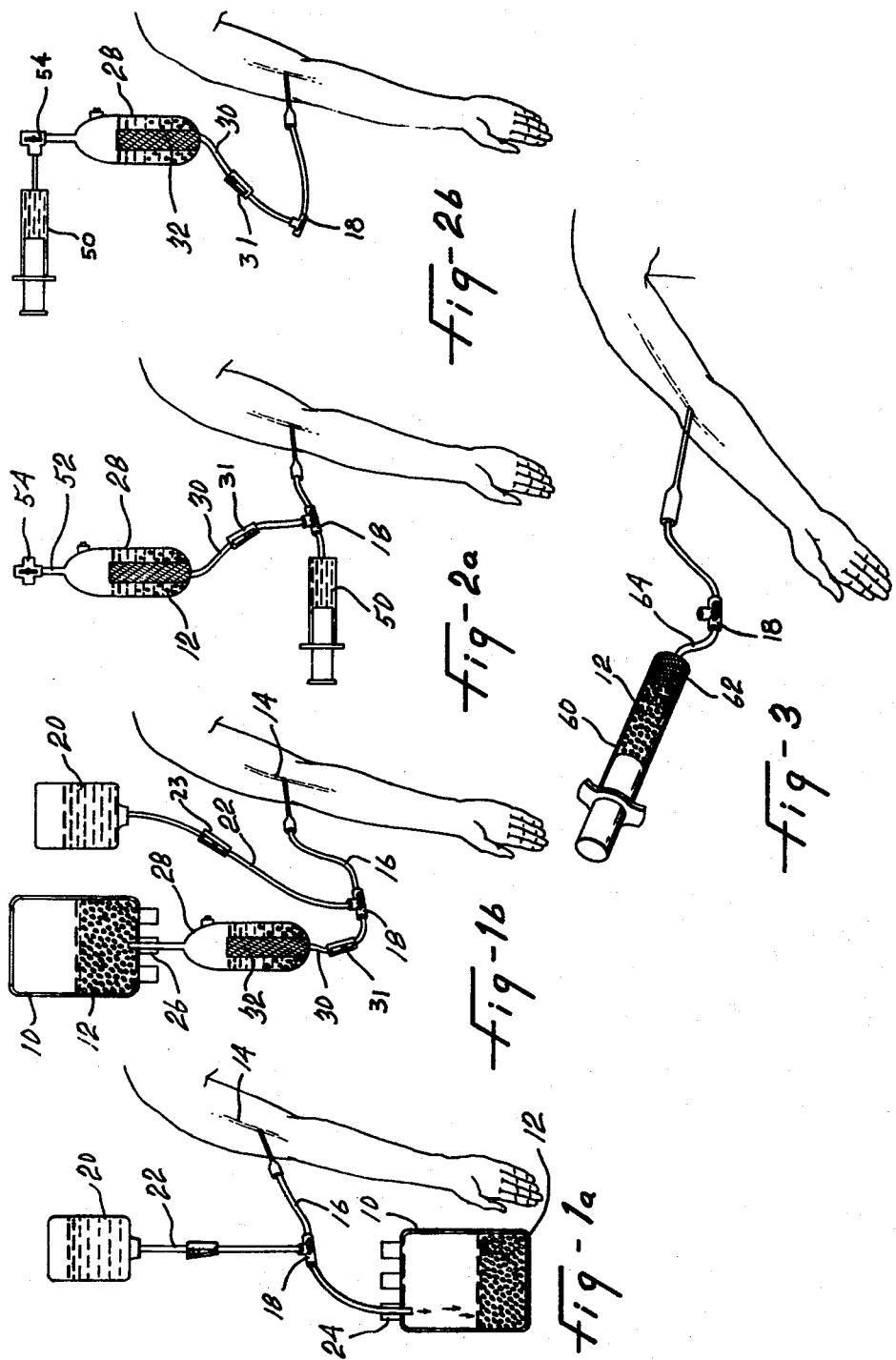

METHOD AND APPARATUS FOR EXTRAVASCULAR TREATMENT OF BLOOD

The present invention relates to a novel method for the extravascular purification of blood to remove a substantial amount of lipoproteins therefrom thereby rendering the blood suitable for return to the blood stream of the patient suffering from abnormally high levels of lipoproteins (lipids). The invention also relates to an apparatus for the extravascular or extracoporeal treatment of blood containing abnormally high levels of lipoprotiens to substantially reduce said amount of lipoproteins to a more compatible level.

PRIOR ART

It is known that millions of individuals are affected by hyperlipemia and hypercholesteremia. These diseases are caused by excess lipids bound to proteins to form macromolecular complexes called lipoproteins. Presently, treatment of the diseases has involved the use of lipotropic agents such as LUFA ® sold by Arlington Laboratories, Division, U.S.V. Inc. or antihyperlipidemic agents such as clofibrate sold under the trade mark ATROMID-S ® by Ayerst Laboratories. Also any chemical treatment of these diseases must be accompanied by special diets which are restricted in all common sources of fat. Though these procedures are relatively useful they do not provide a satisfactory answer because they fail to provide the removal of the excess lipoproteins (lipids) present in the serum.

It is also known that methods and apparatus have been proposed for the extracorporeal treatment of blood containing certain undesirable substances, such as for example, drugs whereby the undesirable substances can be removed by filtration. For example, Yatzidis, H., in *Proc. Europ. Dial Transplant Ass.* 1:83, 1964. demonstrated that the blood of individuals, who had taken an overdose of drugs, could be subjected to an extracorporeal filtration through activated charcoal to remove the excess drug. This method requires heparinisation of the patient, and an external system for causing the blood to flow from and to the body through capsules containing activated charcoal. Unfortunately, this system and others developed along the same lines subsequently cause certain potentially harmful effects, some of which are the removal of glucose, calcium, and certain formed elements (See Duvea et al., *Trans Amer. Soc. Artif. Int. Organs.* 11:178, 1965). Further, it is necessary to heparinate the patient. Finally, it has also been found that such activated charcoall filters have a tendency to block.

Accordingly, it would appear highly desirable to provide a system where the blood of patients suffering from hyperlipemia or hypercholesteremia could be withdrawn for treatment to reduce the lipoprotein content thereof and returned to the patient without danger and discomfort to the patient.

THE INVENTION

In accordance with the present invention, there is provided a method and an apparatus whereby blood of hyperlipemic or hypercholesteremic patients can be withdrawn, chemically treated to reduce the lipoprotein (lipids) content thereof and returned to the patient thereby reducing the general average content of lipoproteins in the thus treated patient.

The novel method of the present invention comprises withdrawing an amount of blood from a patient suffering from hyperlipemia or hypercholesteremia, contacting said withdrawn amount of blood with a divalent metallic ion complex of a sulfated polysaccharide coupled to an activated non-sulfated polysaccharide gel having its remaining active sites blocked (hereinafter referred to as 'the complex gel') whereby a substantial amount of the undesired $\beta$ and pre-$\beta$ lipoproteins are chemically bonded to the complex gel, and then filtering the thus treated blood to remove the complex gel thus obtaining blood wherein the original amount of $\beta$ and pre-$\beta$ lipoproteins have been substantially reduced. Subsequently, the thus treated block is returned to the patient in the usual manner thus providing a substantial reduction of the lipoproteins (lipids) in the total blood volume of the patient. It can be easily appreciated that by repeating this method over a period of a few days to a few weeks will result in reducing the lipoprotein content of hyperlipemic or hypercholesteremic patients to a more acceptable level.

As can be appreciated by those skilled in the art, the novel method of the present invention provides many distinct advantages over the treatment of hyperlipemic or hypercholesteremic patients by the use of chemical agents. As a first advantage, there is no necessity to hospitalize the patient, the method being adapted for treatment of any patient in any out-patient clinic. Further, because of its simplicity, the method of the present invention can be carried out by technicians such as nurses rather than highly specialized medical personnel such as doctors. The apparatus used for carrying out the process of the present invention is simple, inexpensive and can be readily assembled.

A further advantage of the method of the present invention is that it selectively binds the undesirable $\beta$ and pre-$\beta$ lipoproteins which are present in the form of cholesterol, triglycerides and phospholipids while the alpha lipoproteins are not significantly reduced thus allowing said alpha lipoproteins to be returned to the blood stream of the patients. The significant importance of this feature is that it is believed that the alpha lipoproteins play a significant beneficiary role in liberating deposited tissular cholesterol, thus possibly rendering more cholesterol available for removal in subsequent treatments, while the removal of the $\beta$ lipoproteins which are known to carry large amount of cholesterol and pre-$\beta$ lipoproteins which are known to carry large amount of triglycerides can only prove beneficial to any hyperlipemic or hypercholesteremic patient.

Finally, it should also be appreciated that other important factors normally found in blood are not affected by the method of the present invention. Thus, the total proteins, urea nitrogen (BUN), glucose, total bilirubin, electrolytes such as sodium and potassium as well as calcium and magnesium and proteins such as albumin, $\alpha_1$-globulins, $\alpha_2$-globulins, $\beta$-globulins, $\gamma$-globulins and the albumin:globulins (A/G) ratio remain substantially unchanged in the portion of the treated blood. Also, it has been noted that there is no significant change in the enzymes and hormones, red cells, white cells and platelets after treating the blood from hyperlipemic or hypercholesteremic patients in accordance with the present invention.

One of the critical elements in exercising the method of the present invention is the divalent metallic ion complex of a sulfated polysaccharide coupled to an activated nonsulfated polysaccharide gel having its remaining sites blocked. This complex compound is prepared from non-sulfated polysaccharide gel through a series of chemical reactions whereby there is obtained a complex gel which possesses the unique property of selectively binding $\beta$ and pre-$\beta$ lipoproteins.

Generally speaking, the complex gel used in the process of the present invention is prepared by activating a non-sulfated polysaccharide gel, for example with a cyanogen halide, reacting the activated non-sulfated polysaccharide gel with a sulfated polysaccharide, blocking the remaining sites with a chemical blocking agent and finally causing the product obtained to react with a divalent metallic ion thereby forming a divalent metallic ion complex of a sulfated polysaccharide coupled to an activated non-sulfated polysaccharide gel having its remaining sites blocked.

As starting non-sulfated polysaccharide there may be used a polysaccharide or its derivative which is water-insoluble when in matrix form such as a gel. Such polysaccharides are characterized by a molecular weight of at least 30,000. As an example of suitable polysaccharides there may be mentioned, agarose, dextran cellulose and those derived from lactose and glucose. The critical feature of this starting polysaccharide is that it must be non-sulfated thereby leaving its highly reactive sites available for subsequent coupling by activation to sulfated polysaccharide units.

The activation of the non-sulfated polysaccharides is carried out by reaction with a cyanogen halide, for example, cyanogen bromide or cyanogen chloride, by techniques which are known in the art and such as are disclosed in British Patent 1,404,507, Pharmacia Fine Chemicals AB. The thus obtained activated non-sulfated polysaccharide is then reacted with a sulfated polysaccharide of the same type as described above whereby the cyanogen activated sites of the starting polysaccharide will react favourably with the sulfated polysaccharide, thus leaving secondary reaction sites on the starting polysaccharide available for blocking by treatment with a blocking agent such as ethanolamine. The thus obtained product is then reacted with a divalent metallic salt thereby forming the corresponding divalent metallic ion complex. As an example of the divalent metallic ions that can be used there may be mentioned calcium, magnesium or manganese and the like. It should be appreciated that when the term "gel" is used herein it is intended to cover the product in the form of beads, filaments or fibers.

As the starting agarose gel there may be used one which is manufactured and sold by Pharmacia Fine Chemicals AB, Uppsala, Sweden under the trade mark SEPHAROSE ® or by Bio-Rad Laboratories, Richmond, California under the trade mark BIO-GEL ®. Agarose is a linear polysaccharide which consists of alternating residues of D-galactose and 3,6-anhydro-L-galactose units. This product is available in commerce as gel beads and is particularly recommended for use in gel filtration, also referred to as gel chromatography or molecular (particle) sieve chromatography, of high molecular weight proteins and polysaccharides, nucleic acids and viruses. Agarose has at least the same good gelling properties as agar, the gelling being attributed to hydrogen bonding. Agarose gel is prepared from agarose according to a modification of the method described in *Biochem, biophys. Acta.* 79 (1964) 393–398, Hjertén.S. Various types of agarose gels are available on the market and the type suitable for exercising the process of the present invention is the agarose gel which has been treated with cyanogen bromide and the gel which is available as "CNBr-activated SEPHAROSE ® 4b" from Pharmacia Fine Chemicals has been found to be suitable.

As an example of sulfated polysaccharides suitable for the purpose of the present invention there may be mentioned sodium heparin sulfate and sodium dextran sulfate.

The thus prepared divalent metallic ion complex of a sulfated polysaccharide coupled to a CNBr-activated agarose gel having its remaining active sites blocked is in the form of micro beads having a diameter varying between the range of from 40 to 300 microns, and possesses the ability to immobilize certain lipoproteins contained in abnormal amounts in the blood of hyperlipemic or hypercholesteremic patients, thus reducing the lipoprotein content of the blood after filtration of the insolubilized lipoproteins.

In practice a quantity of blood depending upon the weight of the patient is withdrawn, for example, from about 5 to about 500 ml and caused to react with a suitable amount of divalent metallic ion complex of a sulfated polysaccharide coupled to an activated gel non-sulfated polysaccharide in bead form dispersed in a heparin solution whereby a substantial portion of the $\beta$ and pre-$\beta$ lipoproteins of the blood are selectively reacted with the divalent metal complex gel and thus rendered insoluble and after this reaction has taken place causing the blood to be filtered thereby obtaining blood wherein the amount of lipoprotein has been substantially reduced and thereafter returning the thus treated blood to the patient in the usual manner.

The amount of complex gel will usually vary between 20 and 60 grams per 100 cc of blood. The complex gel is dispersed in a heparin solution as is usually done for blood transfusion to avoid coagulation of the blood. The time of contact of the complex gel and the blood is usually between 3 and 5 minutes though longer or shorter time can be used depending on the original lipoprotein content.

The present invention is also concerned with the provision of a novel apparatus for carrying out the above described method. Basically, the apparatus comprises, in combination, blood recipient means containing therein a divalent metallic complex of sulfated polysaccharide coupled to an activated non-sulfated polysaccharide gel support, and filter means for separating the treated blood from the complex gel support to which the lipoproteins have been fixed. These filter means must be provided with a porosity such that passage of the complex gel support therethrough is prevented and only the treated blood may be returned to the patient.

In one form of the apparatus in accordance with the present invention, blood is withdrawn from a patient's vein by means of a catheter and drained into a transfusion bag containing the complex gel support. After the fixing of the $\beta$ and pre-$\beta$ lipoproteins to the complex gel, treated blood is infused back to the patient after having gone through a series of filtering surfaces having pores allowing passage of treated blood only.

In another form of the apparatus in accordance with the present invention, blood is first collected with a syringe which is, then, connected to a bag containing therein the complex gel support and the filter. This bag is provided with outlet means for infusing the blood back to the patient after it has been treated in the presence of complex gel and passed through the filtering surfaces.

In a third form of the apparatus of the present invention, a syringe is provided with the complex gel and the filter therein. The syringe is thus used for collecting blood, treating it, filtering it and returning treated blood to the patient.

In order that the invention be more readily understood, several embodiments thereof are described below solely by way of non-limiting illustrative examples with reference to the accompanying drawings, wherein:

FIGS. 1a and 1b are sketches illustrative of a first embodiment of the apparatus of the present invention, showing respectively the blood collection and the blood infusion steps;

FIGS. 2a and 2b are sketches illustrative of a second embodiment of the apparatus of the present invention, showing respectively the blood withdrawal and the blood infusion steps; and FIG. 3 illustrates a third embodiment of the apparatus of the present invention.

The method of the present invention will be best understood with reference to the accompanying drawings which illustrate various techniques and apparatus for the extravascular treatment of blood containing abnormally high level of lipoproteins.

Referring to FIGS. 1a and 1b, there is shown a first embodiment of the apparatus of the present invention. A blood transfusion bag 10 contains therein a divalent metallic complex of sulfated polysaccharide coupled to an activated non-sulfated polysaccharide gel 12. Blood to be treated is drained from a patient's vein 14 by means of catheter means 16. As illustrated in FIG. 1a, blood withdrawl may be carried out by gravity. When a desired amount of blood is received in bag 10, a stopcock 18 cutss the blood flow to the bag. Stopcock 18 may also be connected to a heparinized saline bag 20 through its outlet tube 22. The inlet port 24 of bag 10 is then sealed off. Outlet port 26 of bag 10 is then connected to a filtering device 28 having an outlet tube 30 connected to the stopcock 18 and equipped with a flow controlling device 31. Prior to the infusion of treated blood back to the patient, stopcock 18 may be opened to allow the liquid inside bag 20 to drip slowly to prevent coagulation in the catheter 16, the drip being controlled by device 23. For blood re-infusion, bag 10 is raised higher than the patient: stopcock 18 is then operated to allow the flow between bag 10 and that patient's vein. The complex gel 12 now reacted with lipoproteins (lipids) as a result of the reaction inside bag 10 pass with the treated blood in the filtering device 28. One important feature of the present invention is the provision of a filter which will have a porosity such that the complex gel reacted with lipoproteins (lipids) will remain in the filtering device 28 whereas the treated blood only will pass to the outlet tube 30. It is preferable to have a filter of a large surface area so that, as the lipoprotein complex gel accumulates around filter 32 at the bottom of filtering device 28, treated blood will still be able to pass through the upper portion of the filter and exit through outlet tube 30. Also, preferably, filter 32 should consist of a series of successive layers of filtering surfaces having pores of decreasing size with the layer having the lowest size of pores being the innermost layer.

Particularly satisfactory results have been obtained with a blood filtering device known under the trademark INTERSEPT ® and disclosed in Belgium Patent No. 827,749 issued to Johnson & Johnson and Puralator Inc. Oct. 9, 1975. Such filter device includes three filtering layers where the outside layer in contact with the complex gel has a pore size of 170 microns; the second and third layers have respectively 40 and 20 microns. As indicated above, the complex gel prepared from agarose beads may have a diameter varying between 40 and 300 microns. It is therefore believed that such filter device is sufficient to prevent passage of any lipoprotein-complex gel reaction product or any unreacted complex gel from reaching the outlet tube 30.

Referring to FIGS. 2a and 2b, a second embodiment of the apparatus of the present invention consists in connecting a syringe 50 to the stopcock 18 described above. In this embodiment, a second stopcock 54 is connected to the inlet tube 52 of the filtering device 28. In operation, a predetermined quantity of blood is collected from the patient's vein 14 into syringe 50. Stopcock 18 is then closed and the syringe is connected to stopcock 54. As illustrated in FIG. 2b, blood is then injected into the filtering device 28. However, in this case, the complex gel is already in the filtering device 28. Blood from syringe 50 mixes with the complex gel and is treated. Opening stopcock 18 and operating on device 31, treated blood is returned to the patient's vein.

Referring to FIG. 3, for treating only a small volume of blood such as for newborns, a syringe type container 60 may be used wherein the complex gel 12 and a filter device 62 having the porosity characteristics described above are provided. Filter 62 is located adjacent the end of container 60 which is connected to the outlet tube 64 which also serves as the inlet tube for blood collection. When treated blood is returned to the patient's vein, filter 62 blocks the complex gel and allows passage of treated blood only. It should be understood, however, that this embodiment should preferably be used for only a small quantity of blood since the complex gel reacted with lipoproteins forms a cheese-like structure which, for a large volume of blood would block the flow of treated blood back to the outlet tube 64.

Although the apparatus above has been described in relation to three specific forms of the invention, it will become apparent to those skilled in the art that it may be varied and refined in various ways. For example, there may be provided a blood recipient bag wherein the complex gel and the filter device are both present therein as a unit. In such device, the filter could be mounted adjacent the inlet of the bag whereby blood to be treated would first pass through the filter before reacting with the complex gel. Then, for blood re-infusion, the bag would merely be inverted and treated blood would again pass through the filter and return to the patient via the inlet of the bag. Other arrangements of filter-and-gel in a bag may easily be envisaged.

The present invention will be more fully understood by referring to the following Examples which are given to illustrate the invention rather than limit its scope.

EXAMPLE 1

A. PREPARATION OF HEPARIN AND DEXTRAN SULFATE-AGAROSE BEAD COMPLEX

1. Activation of agarose beads

Two types of activated agarose beads were used. CNBr-activated SEPHAROSE ® (diameter 40–190μ) was purchased from Pharmacia Fine Chemicals. BIOGEL ® A-5m (diameter 149–297μ) was purchased from Bio-Rad laboratories and then activated with cyanogen bromide (K and K Laboratories) according to the method of *Axén et al* (*Nature* 214:1302, 1967). One hundred g rows of hydrated BIOGEL ® A-5m was reacted with 20 g of cyanogen bromide at 20° C and pH 11.0 with constant stirring. The reaction is usually complete in approximately 10 minutes. Free cyanogen bromide which is hazardous was then removed by washing the gel on sintered-glass filter with 10 liters of sodium bicarbonate buffer. It is also possible to purchase CNBr-activated agarose beads from Pharmacia Fine Chemicals under the trade mark "CNBr-activated SEPHAROSE ® 4B".

2. Coupling of heparin sulfate and dextran sulfate to CNBr-activated agarose beads.

The following sulfated polysaccharides were used: (1) Sodium heparin sulfate obtained K and K Laboratories and (2) Sodium dextran sulfate. (M.W. 500,000) purchased from Pharmacia Fine Chemicals. Both substances were coupled to CNBr-activated agarose beads according to the method of Iverius (Biochem. J., 124:677, 1971). One to two grams of each of sodium heparin sulfate and sodium dextran sulfate are respectively dissolved in bicarbonate buffer and stirred at 4° C with 100 g of hydrated CNBr-activated agarose beads for 16 hours. The remaining active groups on the gel were blocked by stirring for 4 hours with 12 ml of ethanolamine. The gel was finally transferred to sintered-glass filter and washed consecutively with 2 liters of distilled water, 1 liter of 0.5 M sodium chloride. The gel was then transferred to another sintered-glass filter (previously autoclaved to remove pyrogens) and then washed with 10 liters of pyrogen free water. The gel was then stored in autoclaved bottles with rubber sealed-caps at 4° C. This preparation was sterilized with 500 rads of gamma radiation before using for the treatment of human blood.

B. PRECIPITATION AND FILTRATION OF LIPOPROTEINS

Twenty grams of each of the products obtained in Step A.2 was introduced into a blood transfusion bag (Blood Pack Unit) and then 3 ml of 10% $CaCl_2$ solution (depending upon the amount of blood to be withdrawn the final concentration of $CaCl_2$ should be between 0.02 to 0.04 M) was injected into the bag. 100 ml of blood was withdrawn into bag (by vein-puncture and collected by gravity as shown in FIG. 1a). Blood was mixed with gentle agitation of the bag. Under these conditions both beta and pre-beta lipoproteins are selectively complexed with each complex gel.

C. REINFUSION OF BLOOD

The treated blood is reinfused into the patient as shown in FIG. 1b. The blood transfusion bag 10 is raised higher than the patient as for usual transfusion procedure and the blood is allowed to flow through filter 28 which retains the insoluble lipoproteins bound to the complex gel obtained in Step B and allows the blood to flow into the patient through the same vein puncture. The withdrawal of blood, captation of lipoproteins and reinfusion of blood takes about 10 to 20 minutes.

EXAMPLE 2

Human blood treated in accordance with Part B of Example 1 was submitted to various tests and the results obtained are reported in Tables I to V.

TABLE I
IN VITRO PRECIPITATION OF CHOLESTEROL IN HUMAN BLOOD OF NORMOCHOLESTEROLEMIC PATIENT
(Heparin-Sulfate coated agarose beads)

|  | BEFORE | AFTER |
|---|---|---|
| PATIENT 1 | | |
| Cholesterol (mg %) | 206 | 184 |
| Triglycerides (mg %) | 246 | 219 |
| Phospholipids (mg %) | 174 | 155 |
| PATIENT 2 | | |
| Cholesterol (mg %) | 216 | 69 |
| Triglycerides (mg %) | 255 | 114 |
| Phospholipids (mg %) | 260 | 116 |

It will be noted that there is a significant decrease in the blood cholesterol and triglyceride levels.

Human blood treated in the manner described in Example 1 and was submitted to biochemicals and hematological tests and the results for such test are reported in Tables II, III, IV and V.

TABLE II
IN VITRO PRECIPITATION OF CHOLESTEROL IN HUMAN BLOOD OF A HYPERCHOLESTEROLEMIC PATIENT
(Dextran-Sulfate coated agarose beads)

|  | BEFORE | AFTER |
|---|---|---|
| Cholesterol (mg %) | 339 | 129 |
| Triglycerides (mg %) | 172 | 127 |
| Phospholipids (mg %) | 240 | 153 |

TABLE III
ENZYMES AND HORMONES

|  |  | BEFORE | AFTER |
|---|---|---|---|
| SGOT | (Serum glutamic oxalacetic transaminase) | 17 | 16 |
| SGPT | (Serum glutamic pyruvic transaminase) | 21 | 17 |
| SLDH | (Serum Lactic Dehydrogenase) | 181 | 150 |
| Cortisol | (mcg %) | 19 | 16 |

TABLE IV
BIOCHEMICAL PROFILE

|  | BEFORE | AFTER |
|---|---|---|
| Total proteins (g %) | 7.8 | 6.7 |
| Nitrogen urea (mg %) | 14.0 | 12.8 |
| Glucose (mg %) | 94.0 | 102 |
| Total bilirubin (mg %) | 0.8 | 0.46 |
| Electrolytes | | |
| Sodium (meq/L) | 138 | 142 |
| Potassium (meq/L) | 4.1 | 4.7 |
| Protein electrophoresis | | |
| Albumins | 55.2 | 58.7 |
| $\alpha_1$-globulins | 3.7 | 2.8 |
| $\alpha_2$-globulins | 9.0 | 8.3 |
| $\beta$-globulins | 15.7 | 10.9 |
| $\alpha$-globulins | 14.6 | 18.4 |
| Ratio A/G | 1.23 | 1.42 |

TABLE V
HEMATOLOGY

|  | BEFORE | AFTER |
|---|---|---|
| R.B.C's ($\times 10^6$) | 5.41 | 5.46 |
| Hb (g %) | 16.5 | 16.60 |
| Hct (%) | 47.3 | 45.4 |

EXAMPLE 3

By proceeding in the same manner as in Example 1 but with animal blood, the following analytical results are obtained.

TABLE VI
BIOCHEMICAL PROFILE

| | DOG-222 | | DOG-333 | |
|---|---|---|---|---|
| | before filtration | after filtration | before filtration | after filtration |
| Total proteins (g%) | 5.5 | 4.3 | 6.5 | 5.1 |
| Globulins (g%) | 3.4 | 2.9 | 3.4 | 2.9 |
| Albumins (%) | 43.5 | 43.7 | 60.0 | 60.0 |
| $\alpha_1$-globulins (%) | 7.2 | 8.4 | 4.8 | 4.9 |
| $\alpha_2$-globulins (%) | 14.9 | 17.1 | 13.0 | 14.2 |
| $\beta$-globulins (%) | 28.7 | 22.1 | 11.0 | 11.0 |
| $\alpha$-globulins (%) | 5.6 | 7.7 | 10.6 | 10.0 |
| Ratio A/G | 0.8 | 0.8 | 1.52 | 1.50 |
| Total bilirubin (mg%) | 0.4 | 0.3 | — | — |
| Glucose (mg%) | 142 | 122 | 113 | 129 |

TABLE VII
ENZYMES AND HORMONES

| | | DOG-222 | | DOG-333 | | DOG-444 | |
|---|---|---|---|---|---|---|---|
| | | before filtration | after filtration | before filtration | after filtration | before filtration | after filtration |
| Alkaline Phosphatase | | 60 | 49 | 10 | 9 | — | — |
| SGOT | (Serum glutamic oxalacetic transaminase) | 19 | 17 | — | — | — | — |
| SGPT | (Serum glutamic pyruvic transaminase) | 17 | 15 | — | — | — | — |
| SLDH | (Serum Lactic Dehydrogenase) | 99 | 133 | — | — | — | — |
| Cortisol | (mcg %) | — | — | — | — | 24 | 26.5 |

TABLE VIII
ELECTROLYTES

| | DOG-222 | | DOG-333 | | DOG-444 | |
|---|---|---|---|---|---|---|
| | before filtration | after filtration | before filtration | after filtration | before filtration | after filtration |
| Sodium (mEq/L) | 145 | 147 | 145 | 146 | 142 | 147 |
| Potassium (mEq/L) | 4.0 | 3.4 | 4.1 | 3.6 | 4.0 | 3.7 |
| Chlorides (mEq/L) | 110 | 118 | 119 | 123 | 120 | 122 |
| Calcium (mg %) | 11.4 | 11.8 | 9.9 | 10.6 | 9.3 | 10.4 |
| Magnesium (mg %) | 1.6 | 1.6 | 1.0 | 0.8 | 2.0 | 1.7 |

TABLE IX
HEMATOLOGY

| | DOG-222 | | DOG-333 | | DOG-444 | |
|---|---|---|---|---|---|---|
| | before filtration | after filtration | before filtration | after filtration | before filtration | after filtration |
| W.B.Cs ($\times 10^3$) | — | — | 7.3 | 4.1 | — | — |
| R.B.Cs ($\times 10^6$) | — | — | — | — | — | — |
| Hb (g %) | 17.0 | 13.8 | 18.8 | 19.2 | 13.8 | 11.3 |
| Hct (%) | 48.0 | 40.0 | 52.0 | 53.5 | 40.0 | 34.0 |
| Platelets ($\times 10^3$) | 180 | 39 | abundant | abundant | 180 | 101 |

TABLE X
DOG CONTROL*

| | DOG C-111 | | DOG C-222 | |
|---|---|---|---|---|
| | before | after | before | after |
| Total proteins (g %) | 6.1 | 5.5 | 5.3 | 4.9 |
| Globulins (g %) | 3.6 | 3.5 | 3.4 | 3.3 |

*The other biochemical parameters are unchanged.

What is claimed is:

1. A method for the extracorporeal treatment of the blood of a patient afflicted with hyperlipemia and/or hypercholesteremia to effect a reduction of the $\beta$ and pre-$\beta$ lipoproteins in said blood without substantially affecting the remaining constituents of the blood, which comprises:
   (a) withdrawing a portion of blood from said patient,
   (b) contacting said blood portion with a water-insoluble gel of a sulfated polysaccharide coupled to an activated non-sulfated polysaccharide having its remaining sites blocked, in the presence of calcium cation in a concentration of 0.02 to 0.04M, thereby selectively binding a substantial portion of the beta and pre-beta lipoproteins with the calcium complex gel,
   (c) causing the thus treated blood portion to be filtered, thereby to separate the treated blood portion from the complex gel, whereby there is obtained the same blood portion wherein the initial amount of beta and pre-beta lipoproteins has been substantially reduced without affecting the remaining constituents of the blood, and
   (d) returning the thus filtered blood portion to the patient.

2. The method of claim 1, wherein the sulfated polysaccharide is heparin sulfate.

3. The method of claim 1, wherein the sulfated polysaccharide is dextran sulfate.

4. The method of claim 1, wherein the non-sulfated polysaccharide is agarose.

5. In an apparatus for removing a substantial amount of $\beta 0$ and pre-$\beta$ lipoproteins from blood comprising recipient means for receiving therein blood to be treated; means allowing the removal of treated blood from said recipient means; and filter means disposed between said gel support and said means allowing treated blood removal, the improvement comprising a calcium metallic complex of sulfated polysaccharide coupled to an activated non-sulfated polysaccharide gel support wherein the remaining sites are blocked being contained in said recipient means whereby, when in the presence of said gel support, said blood is treated by the fixing of a substantial amount of $\beta$ and pre-$\beta$ lipoproteins to said support and said filter means having a porosity such as to prevent passage of said gel support therethrough as said treated blood is withdrawn from said recipient means.

6. An apparatus as defined in claim 5, wherein said gel support consists of agarose beads coated with heparin.

7. An apparatus for removing a substantial amount of $\beta$ and pre-$\beta$ lipoproteins from blood as claimed in claim 5, further comprising inlet means allowing blood to be treated to be received in said recipient means and outlet means allowing the removal of treated blood from said recipient means; and said filter means being disposed between said gel support and said outlet means.

8. An apparatus for removing a substantial amount of $\beta$ and pre-$\beta$ lipoproteins from blood as claimed in claim 5, further comprising said recipient means having inlet means for receiving therein blood to be treated and outlet means for allowing the removal of treated blood from said recipient means; said filter means being connected to said outlet means; and further outlet means connected to said filter means for further discharging treated blood after having passed through said filter means.

9. An apparatus for removing a substantial amount of $\beta$ and pre-$\beta$ lipoproteins from blood as claimed in claim 5, further comprising outlet means connected to said recipient means; said filter means being received in said recipient means and disposed between said gel support and said outlet means, said filter means having a porosity such as to prevent passage of said gel support therethrough as said treated blood passes through said outlet means.

10. An apparatus as defined in claim 9, wherein said recipient means includes inlet means allowing blood to be treated to be received therein; further comprising syringe means for collecting blood from a patient's vein; said syringe means being adapted to be connected to said inlet means for discharging blood to be treated in said recipient means.

11. An apparatus as defined in claim 10, said outlet means including catheter means for returning treated blood to the patient; said outlet means further comprising stopcock means connected to said catheter means whereby said syringe means may be connected to said stopcock means for the withdrawal of blood to be treated from said vein.

12. An apparatus for removing a substantial amount of $\beta$ and pre-$\beta$ lipoproteins from blood as claimed in claim 5, further comprising means for withdrawing blood from a patient's vein; and tube means for conducting blood collected from said vein to said recipient means; said filter means being disposed between said gel support and said tube means; said filter means having a porosity such as to prevent passage of said gel support therethrough as said treated blood is returned to said vein through said tube means.

13. An apparatus as defined in claim 5, wherein said filter means have a large surface area in comparison to the volume of blood to be treated.

14. An apparatus as defined in claim 13, wherein said filter means include successive layers of filtering surfaces having pores decreasing in size for the different layers with the smallest porosity being on the filtering surface closest to said means allowing the removal of treated blood.

* * * * *

UNITED STATES PATENT OFFICE
CERTIFICATE OF CORRECTION

Patent No. 4,103,685  Dated August 1, 1978

Inventor(s) Paul J. Lupien, et al

It is certified that error appears in the above-identified patent and that said Letters Patent are hereby corrected as shown below:

In the Abstract, line 2: "anc" should be --and--.

line 5: "polysaccacharide" should be --polysaccharide--.

Column 1, line 11: "extracoporeal" should be --extracorporeal--.

line 13: "lipoprotiens" should be --lipoproteins--.

Column 5, line 32: "withdrawl" should be --withdrawal--.

line 34: "cutss" should be --cuts--.

Column 6, last line, to Column 7, line 1: "One hundred g rows" should be -- 100 g --.

UNITED STATES PATENT OFFICE
CERTIFICATE OF CORRECTION

Patent No. 4,103,685          Dated August 1, 1978

Inventor(s)   Paul J. Lupien, et al

It is certified that error appears in the above-identified patent and that said Letters Patent are hereby corrected as shown below:

Column 10, line 53: "$\beta 0$" should be -- $\beta$ --.

line 59: Cancel "metallic".

In the Title Page, identify the Assignees as Paul J. Lupien and Sital Moorjani

Signed and Sealed this

First Day of May 1979

[SEAL]

Attest:

RUTH C. MASON
Attesting Officer

DONALD W. BANNER
Commissioner of Patents and Trademarks